(12) United States Patent
Senn

(10) Patent No.: US 8,632,235 B2
(45) Date of Patent: Jan. 21, 2014

(54) LIGHT CURING DEVICE

(75) Inventor: Bruno Senn, Buchs (CH)

(73) Assignee: Ivoclar Vivadent AG, Schaan (LI)

( * ) Notice: Subject to any disclaimer, the term of this patent is extended or adjusted under 35 U.S.C. 154(b) by 351 days.

(21) Appl. No.: 12/942,293

(22) Filed: Nov. 9, 2010

(65) Prior Publication Data

US 2011/0141733 A1    Jun. 16, 2011

(51) Int. Cl.
*F21V 5/00* (2006.01)

(52) U.S. Cl.
USPC ............................. 362/572; 362/573; 362/804

(58) Field of Classification Search
USPC .......................................... 362/572, 573, 804
See application file for complete search history.

(56) References Cited

U.S. PATENT DOCUMENTS

| | | | |
|---|---|---|---|
| 1,480,904 A * | 1/1924 | Halvorson, Jr. ............... | 362/305 |
| 6,692,250 B1 | 2/2004 | Decaudin et al. | |
| 6,692,251 B1 | 2/2004 | Logan et al. | |
| 6,695,614 B2 | 2/2004 | Plank | |
| 6,767,109 B2 | 7/2004 | Plank et al. | |
| 7,001,057 B2 | 2/2006 | Plank et al. | |
| 7,207,694 B1 * | 4/2007 | Petrick ........................... | 362/804 |
| 7,300,175 B2 * | 11/2007 | Brukilacchio ................ | 362/555 |
| 7,964,886 B2 | 6/2011 | Fujita et al. | |
| 2001/0046652 A1 | 11/2001 | Ostler et al. | |
| 2002/0151941 A1 | 10/2002 | Okawa et al. | |
| 2002/0187455 A1 | 12/2002 | Melikechi et al. | |
| 2004/0149998 A1 | 8/2004 | Henson et al. | |
| 2004/0248059 A1 | 12/2004 | Katsuda et al. | |
| 2005/0152146 A1 * | 7/2005 | Owen et al. .................. | 362/294 |
| 2005/0231983 A1 | 10/2005 | Dahm | |
| 2006/0226437 A1 | 10/2006 | Fujita et al. | |
| 2007/0134616 A1 | 6/2007 | Gill et al. | |
| 2008/0054288 A1 | 3/2008 | Harrah et al. | |
| 2009/0103296 A1 * | 4/2009 | Harbers et al. ................ | 362/234 |

FOREIGN PATENT DOCUMENTS

DE    10 2004 007 812 A1    9/2005

* cited by examiner

*Primary Examiner* — William Carter
(74) *Attorney, Agent, or Firm* — Ann M. Knab; Thad McMurray

(57) ABSTRACT

The invention relates to a light curing device for dental purposes having a plurality of semiconductor light sources, each light source includes a light-emitting chip, wherein said chips are mounted on a common and chip-cooling substrate. Each chip is surrounded by an individual reflector body connected to the substrate and/or the chip associated therewith, and the reflector bodies of at least two chips are arranged next to one another but are not connected with one another.

18 Claims, 3 Drawing Sheets

LIGHT CURING DEVICE

CROSS-REFERENCE TO RELATED APPLICATIONS

This application claims the benefit of European Patent Application Serial No. 09178725.9, filed Dec. 10, 2009, which is hereby incorporated by reference in its entirety.

TECHNICAL FIELD

The invention relates to a light curing device having semiconductor light sources, and more particularly to a light curing device for use in dental applications.

In prior art light curing devices such as that disclosed in U.S. Pat. No. 6,695,614, which is hereby incorporated by reference, recesses are formed in a common copper substrate, and the recesses receive chips that serve for the emission of light. This solution has the advantage that all chips substantially have the same temperature due to the solid copper substrate, and good heat dissipation is ensured. The light emission, however, in this solution requires improvement due to the small reflectors.

In order to improve the light emission it has been proposed to provide collecting lenses above individual reflectors of this kind. Nevertheless, the light efficiency is not particularly high. This also applies to solutions known from U.S. Pat. Nos. 7,001,057 and 6,767,109, which are hereby incorporated by reference. Here, the reflectors, at least partially, are applied as raised bodies that surround the LED chips in a tight manner.

Moreover, it has already been proposed to use LED lamps with parabolic reflectors, in which case reference is made to, for example, DE 10 2004 007 812 A1, which is hereby incorporated by reference.

Further, it has already been proposed in-house to employ enlarged reflectors that are commonly constructed from one solid body, wherein the individual reflectors intersect one another. Surprisingly, however, the light emission is comparatively unsatisfactory with such a solution so that this solution has not been pursued further.

In particular, with light curing devices for dental purposes, however, light emission must be sufficient and within the specification. An insufficient light emission may lead to the result that the dental material to be polymerized is not fully cured resulting not only in remaining free radicals but in particular in the overall restoration not being sufficient and thus causing regular customer complaints.

SUMMARY OF THE INVENTION

It is therefore an object of an embodiment of the invention to provide a light curing device for dental purposes having a plurality of semiconductor light sources that each comprise a light-emitting chip, wherein said chips are mounted on a common substrate that, in particular dissipates heat. The several chips may be driven separately or together, wherein the light emission is improved in comparison to the multiple arrangements or arrays of LED chips which have been known so far.

It is a further object of an embodiment that each chip is surrounded by an individual reflector body connected to the substrate and/or the chip associated therewith, and at least two reflector bodies are arranged next to one another but are not connected with one another.

According to an embodiment of the invention, the light emission of the inventive light curing device is improved in particular at high performance. According to an embodiment of the invention, high-quality optics shared by all chips may be used, and the light emission thereof surprisingly is close to the theoretical maximum.

According to an embodiment of the invention, the thermal decoupling of the individual reflector bodies may result in the fact that they do not deviate from their predetermined optical axis. This allows the use of highly reflective metal or plastic bodies as reflector bodies, the thermal expansion coefficient of which is comparatively large but nevertheless enables an axis constancy of the reflector. Apparently, the reflector bodies which have an inner parabolic shape, then deform symmetrically without the LED chips departing from the focus, and no axis error arises as it is the case with already known solutions in which the reflectors quasi or partially move outwardly due to the thermal stress, i.e., the expansion.

An especially favorable inventive embodiment thus provides that the adjacent reflector bodies are separated by a gap from one another, said gap preferably extending across the entire separating gap or slit between the adjacent reflector bodies in equal width. It is to be understood that a reflector body may be of metal construction and in this case at the same time provides for a certain cooling function or effect for the heat dissipated, or it may be made of plastic with a corresponding internal metallization.

The gap preferably extends in a straight manner, at least as far as adjacent reflectors are concerned, and in a tangential manner with respect to each associated reflector cone of the reflector body.

In this connection, reflector cone refers to any suitable formed body which has been optimized for the light emission, even if the reflector cone is substantially merely cone-shaped, or parabolic, for example.

In order to improve the heat dissipation with an alternating operation of the LED chips that may also emit different wavelengths, it is possible to connect the reflector bodies if they are of metallic construction, via the substrate mechanically and also thermally.

In this case a large contact surface for the reflector body is preferred that preferably may comprise a significant wall thickness of, for example, ¼ of the diameter of the light emitting surface of each reflector body. It is to be understood that the wall thickness of the individual reflectors may be adapted to the requirements in a wide range of sizes. For example, a wall thickness of ⅓ or ⅕ or ⅙ of the light emission surface of the individual reflector body may be selected or from a range of from about ⅓ to about ⅙ of the light emission surface of the individual reflector body.

It is to be understood that the individual reflector bodies, if needed, may be provided with heat-dissipating means at the exposed outer circumference thereof, for example with cooling fins, or by means of a contact with a large-area heat-dissipating body.

According to an embodiment of the invention it is particularly favorable if the individual reflector bodies, if necessary apart from the area that immediately surrounds the LED chips, are thermally isolated and decoupled from one another such that even in case of a corresponding expansion the individual reflectors do not touch one another.

According to an embodiment of the invention it is particularly favorable if the reflector bodies at least in the cold state are separated from one another through a gap therebetween.

According to an embodiment of the invention it is particularly favorable if each reflector body in particular is of metallic construction and in particular comprises a substantially uniform wall thickness.

According to an embodiment of the invention it is particularly favorable if each reflector body comprises a reflector cone that substantially has an obtuse parabolic inner shape, and that the openings of the reflector bodies on the light exit side are located in one plane and that the LED chips are each arranged in the focus of the parabolic or conic section.

According to an embodiment of the invention it is particularly favorable if each reflector body is connected with the substrate in a positive-locking manner, and in particular comprises at least one protrusion at an end region opposite to the light exit direction, said protrusion engaging into a recess or opening of the substrate.

According to an embodiment of the invention it is particularly favorable if at least one protrusion that faces outwardly from the outer surface of the reflector is provided on each individual reflector, and that in particular protrusions or fins or projections are provided that protrude from the reflector bodies and increase the cooling surface of the reflector body.

According to an embodiment of the invention it is particularly favorable if the individual reflectors are thermally connected to one another through a gap-free and tight fit or rest on the substrate via the substrate.

According to an embodiment of the invention it is particularly favorable if a collecting lens or a transparent cover disk covering the reflector body is arranged on the light exit side opening region of at least one reflector body.

According to an embodiment of the invention it is particularly favorable if the semiconductor light sources are arranged at the front end of a hand-held light curing device.

According to an embodiment of the invention it is particularly favorable if a light-conducting element, in particular in the form of a light-conducting rod, is arranged in the light exit direction after the semiconductor light sources.

According to an embodiment of the invention it is particularly favorable if the semiconductor light sources emit light at a wavelength of 350 to 480 nm and that in particular at least two adjacent light sources emit light of different wavelength.

According to an embodiment of the invention it is particularly favorable if adjacent reflector bodies do not intersect one another and if the wall thickness of the reflector bodies in the direction towards the adjacent reflector body at the top end surfaces thereof is reduced to at least half the wall thickness, in particular to less than $1/10$.

According to an embodiment of the invention it is particularly favorable if each reflector body comprises a uniform wall thickness across at least half of its circumference, said wall thickness in particular amounting to at least $1/8$, preferably approximately $1/4$ of the light exit diameter of the reflector body.

According to an embodiment of the invention it is particularly favorable if at least two and at most five, in particular, at most four reflector bodies are arranged adjacent to one another on a common substrate, preferably, three reflector bodies.

According to an embodiment of the invention it is particularly favorable if the gap between the reflector bodies in the cold state has a width that is calculated so that the reflector body upon transition from the cold to the hot state, protrudes into the gap at most, half the width of the gap.

According to an embodiment of the invention it is particularly favorable if the light curing device at least comprises one sensor that is arranged on the substrate or that is connected with the substrate.

BRIEF DESCRIPTION OF THE DRAWINGS

Further advantages, details and features become apparent from the following description of embodiments of the invention with reference to the drawings, in which.

DETAILED DESCRIPTION

Figure 1:
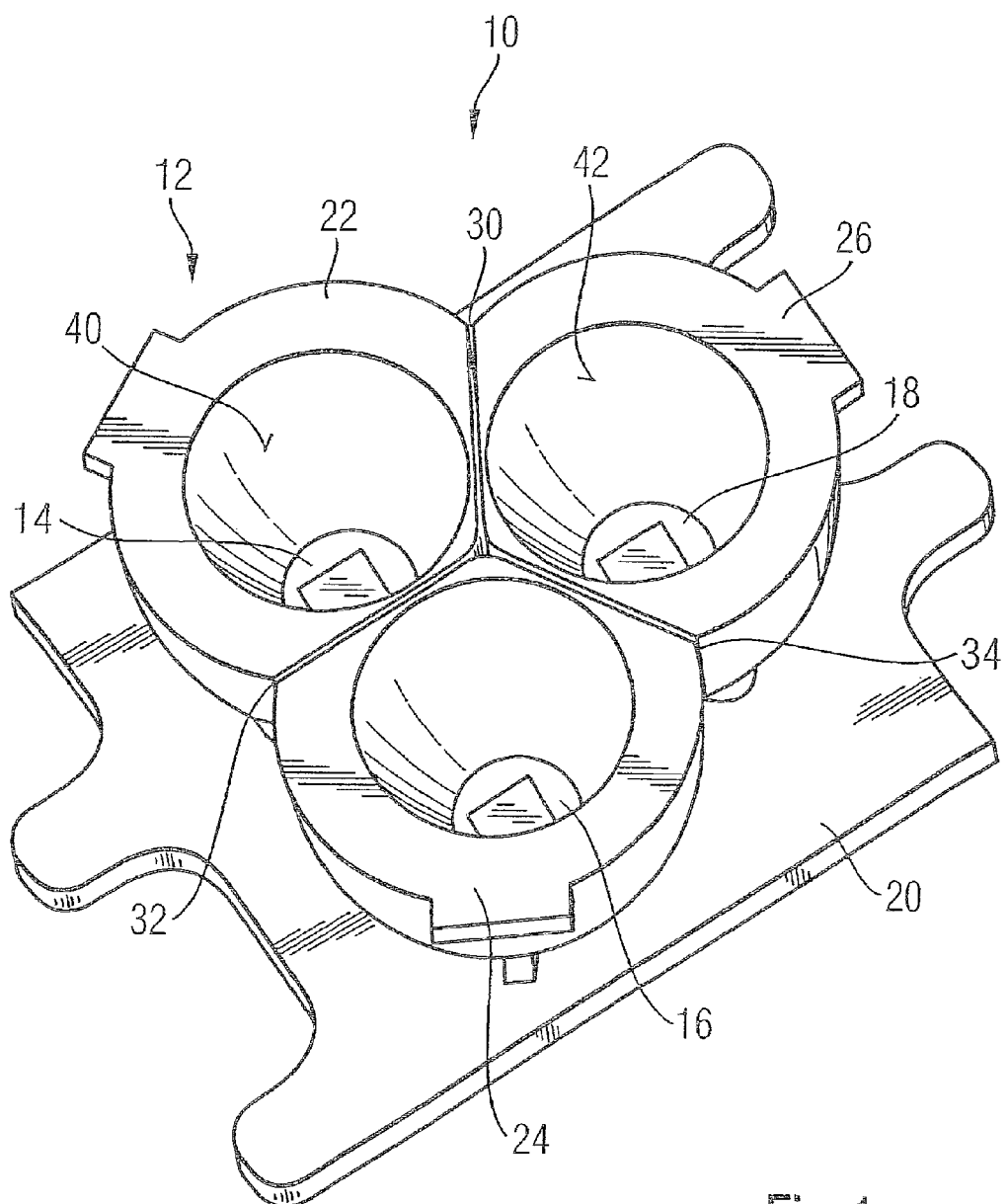
FIG. 1 illustrates a schematic perspective view of the light source of an embodiment of a light curing device for dental purposes according to the invention.

FIG. 1 illustrates a light curing device 10 according to an embodiment of the invention that comprises a light source 12 having a plurality of semiconductor light sources. These include three light-emitting chips 14, 16 and 18 that are mounted on a common and chip-cooling substrate 20. It is preferable that the three light emitting chips 14, 16 and 18 are all identical in their dimensions and shape and are arranged in a cloverleaf-like shape.

Each chip is surrounded by a reflector body, i.e. chip 14 is surrounded by reflector body 22, chip 16 is surrounded by reflector body 24 and chip 18 is surrounded by reflector body 26. The individual reflector bodies 22 to 26 are each supported by the substrate 20 and mounted thereon.

At least above the chips 14, 16 and 18, a gap is provided between the individual reflector bodies 22 to 26, namely gap 30 between the reflector bodies 22 and 26, gap 32 between the reflector bodies 22 and 24 and gap 34 between the reflector bodies 24 and 26. These gaps comprise an inventive width that is selected such that even in case of an enlargement of the individual reflector bodies 22 to 26, the respective gaps 30 to 34 are not bridged, so that the reflector bodies 22 to 26 are always mechanically separated without abutting on one another or engaging with one another.

It is to be understood that the mounting of the individual reflector bodies 22 to 26 on the substrate 20 is selected to be sufficiently dimensionally stable and firm such that an abutment or attachment bridging the gap does not arise even in case of vibrations.

If one of the LED chips 14 to 16, for example, has an edge length of 5 mm, each gap 30 to 34 in the cold state may have a size of 0.5 mm, for example, wherein it is to be understood that the required gap width may be ascertained either by calculation or by experiments.

According to an embodiment of the invention it is provided that the reflector bodies 22 to 26 are manufactured to be quite thick. For example, the wall thickness of the reflector bodies may amount to approximately 4 mm, and it is possible to adapt to the requirements in large areas.

According to an embodiment of the invention the wall thickness of the reflector bodies each is notedly reduced relative to one another in order to provide the gap 30 to 34 in the adjacent areas of the reflector bodies 22 to 26, in particular in the top area, that is to say, in the area of the light exit surface 40 of the individual reflector bodies 22 to 26. At this location for example, the wall thickness may be reduced to gap width or even to half the gap width, wherein according to the invention it is preferred that the individual reflectors do not intersect one another.

Accordingly, each reflector body 22 to 26 preferably comprises a parabola frustrum-shaped or paraboloidal-shaped inner surface 42, wherein, in an embodiment, the LED chips 14 to 18 are each arranged in the focus of the parabola-frustrum shaped inner surface 42. As can be seen from FIG. 1, the light exit openings of each of the individual reflector bodies are arranged very close to each other, comprise a substantially circular shape and said openings do not intersect From FIG. 2 it becomes apparent that the gap 34 between the adjacent reflector bodies 24 to 26 extends to the substrate 20, thus is completely drawn through to the bottom. The third gap is both uniform with respect to width and height such that each LED chip 14 to 18 each remains at its given position irrespective of the movement of the reflector bodies 22, 24 and 26.

Even when the substrate 20 here is illustrated to be a comparatively thin and little compact, it is to be understood that in practice a substantial thermal stress is also present there. Accordingly, the thermal dissipation resistance of the substrate 20 in practice is low which is ensured by providing respective coolants (not illustrated).

According to an embodiment of the invention, due to specific optics that are attached in front of the reflector bodies 22 to 26, the axial position of the LED chips shall not be changed which means that not only a "deflection" of the individual reflector bodies must be prevented.

Figure 2:
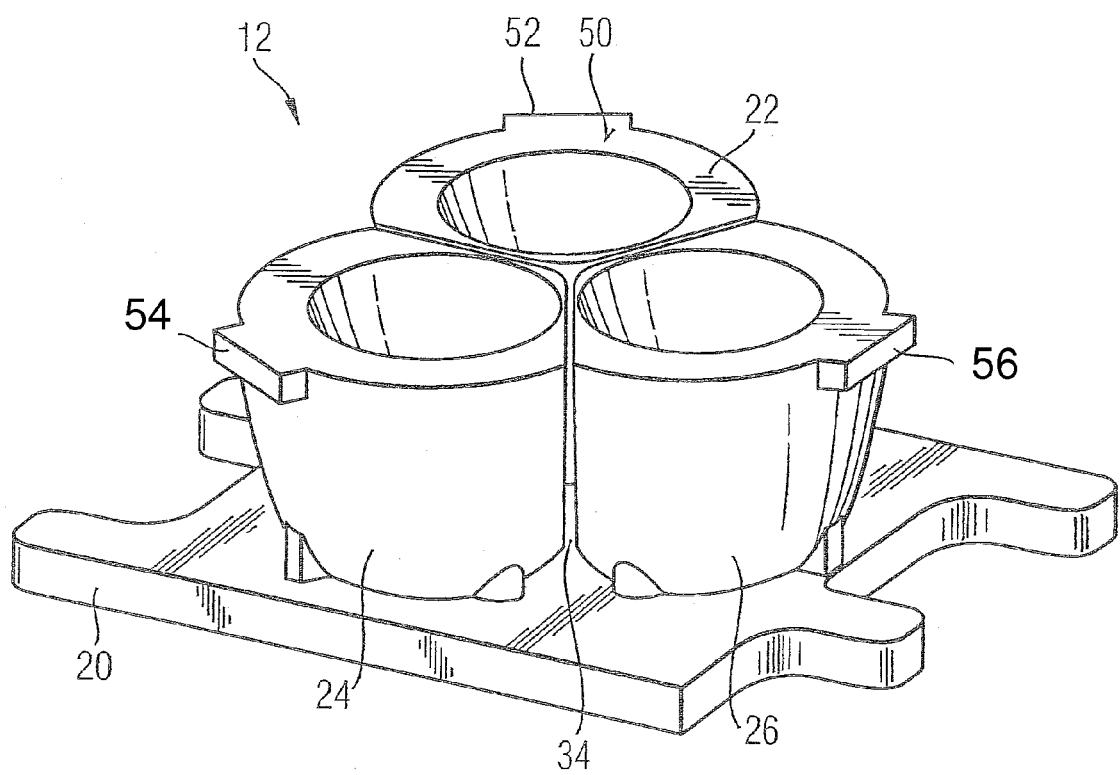
FIG. 2 illustrates a further perspective view of the embodiment of FIG. 1.

Preferably, the light emitting surfaces 40 or the openings on the light exit side of the reflector bodies are arranged in one plane which becomes apparent from FIG. 2. This plane may form a bearing surface 50 either for individual collecting lenses or for a common collecting lens for the light source 12 or for sophisticated optics that concentrates and focuses the light emission in a way that is particularly favorable for the given application purpose, i.e., the light curing process of dental materials.

It is to be understood that a transparent cover disk may be provided instead of the collecting lens or in addition thereto that also serves as a thermal separation between the collecting lens and the reflectors and in this way prevents the deformation of the optics due to a heating of the reflector bodies.

According to an embodiment of the invention, the light source 12 may be arranged both at the front end of a hand-held light curing device and in the base thereof, whereby in the second case it is preferred that a light-conducting rod extends from the light source 12.

It is preferred that protrusions or projections or fins 52, 54 and 56 are provided for the mechanical attachment of the light source 12, wherein the protrusions may be formed at the exterior/front of each individual reflector 22 to 26 and face to the outside and preferably not exceed the above-mentioned plane. At this position, each reflector body 22 to 26 is comparatively cold, as the heat is primarily introduced at the base of each reflector body 22 to 26. The absorption at this position in this respect is also possible without constructively exigent thermal damping measures.

Figure 3:
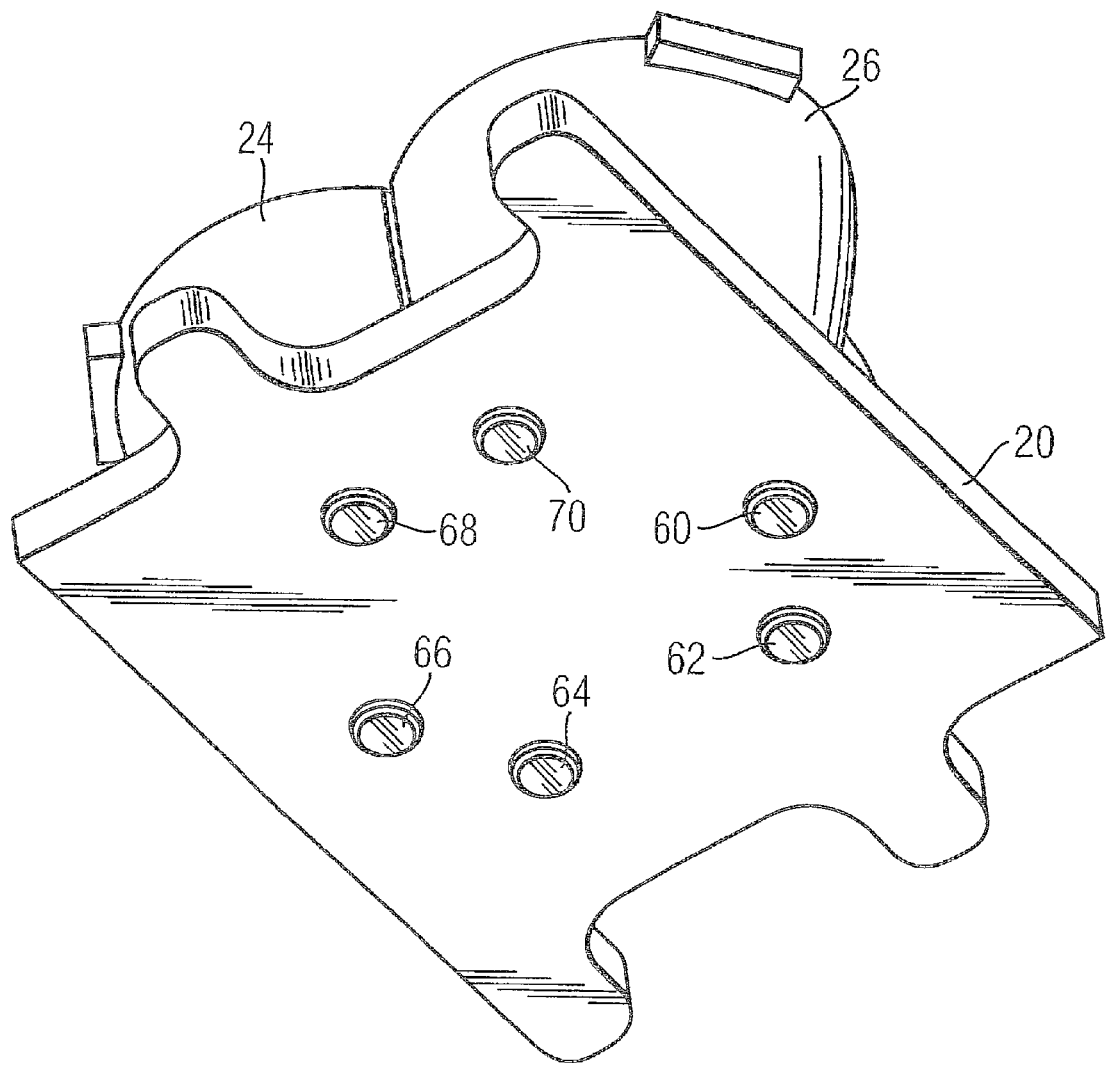
FIG. 3 illustrates a view of the embodiment of FIG. 1, in a view directed obliquely from below.

FIG. 3 shows that the reflector bodies 22 to 26 each comprise downward-facing protrusions 60, 62, 64, 66, 68 and 70, that is, each reflector body 22, 24 and 26, comprises two protrusions that pass through the substrate 20 and which provide for a form-fitting anchorage. In this connection it is particularly favorable if the connecting line between two protrusions of a reflector body, that is, for example, of the protrusions 60 and 70 of the reflector body 26, is below the respective LED chips of the reflector such that a symmetrical guidance is ensured in this respect in case of a possible thermal expansion of the substrate 20.

All numbers expressing quantities or parameters used in the specification are to be understood as additionally being modified in all instances by the term "about". Notwithstanding that the numerical ranges and parameters set forth, the broad scope of the subject matter presented herein are approximations, the numerical values set forth are indicated as precisely as possible. For example, any numerical value may inherently contains certain errors, evidenced by the standard deviation associated with their respective measurement techniques, or round-off errors and inaccuracies.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A light curing device for dental purposes comprising:
a plurality of semiconductor light sources,
wherein each light source comprises a light-emitting chip, wherein the light-emitting chips are mounted on a common substrate that dissipates heat;
wherein each light-emitting chip is surrounded by an individual reflector body connected to the substrate and/or the light-emitting chip associated therewith;
at least two reflector bodies are arranged next to one another but are not connected with one another; and
wherein the individual reflector bodies are mounted on the common substrate, wherein each reflector body comprises a substantially uniform wall thickness except in an area of the reflector body adjacent another reflector body whereat the wall thickness is thinner in order to provide gaps between the individual reflectors bodies.

2. The light curing device as claimed in claim 1, wherein the reflector bodies at least in the cold state are separated from one another by a gap, wherein the gap is straight and tangential with respect to each associated reflector body.

3. The light curing device as claimed in claim 2, wherein the individual reflector bodies are mounted on the common substrate, wherein the gap formed between each adjacent reflector body is not bridged upon expansion of the reflector bodies.

4. The light curing device as claimed in claim 3, wherein each gap between each adjacent reflector body extends from the top to the bottom of the reflector body.

5. The light curing device as claimed in claim 1, wherein each reflector body is of metallic construction and comprises a substantially uniform wall thickness.

6. The light curing device as claimed in claim 1, wherein each reflector body comprises a reflector cone that substantially has a parabolic inner shape, and wherein the openings of the reflector bodies on the light-emitting side are located in one plane.

7. The light curing device as claimed in claim 6, wherein each light-emitting chip is surrounded by an associated individual reflector body, wherein the light-emitting chips are each arranged in the focus of the parabolic shaped inner surface of the respective individual reflector body.

8. The light curing device as claimed in claim 6, wherein at least three reflector bodies are mounted on a common substrate, each of the reflector bodies being identical in dimension and shape, wherein the reflector bodies are arranged in a cloverleaf-shaped manner.

9. The light curing device as claimed in claim 1, wherein each reflector body is connected with the substrate in a positive-locking manner, and comprises at least one protrusion at an end region opposite to the light exit direction, said protrusion engaging into a recess or opening of the substrate.

10. The light curing device as claimed in claim 1, wherein projections are provided that protrude from the outer surface of the reflector bodies and increase the cooling surface of the reflector body.

11. The light curing device as claimed in claim 1, wherein the individual reflectors are thermally connected to one another through a gap-free and tight fit or rest on the substrate via the substrate.

12. The light curing device as claimed in claim 1, wherein a collecting lens or a transparent cover disk is arranged on the light exit side opening region of at least one reflector body.

13. The light curing device as claimed in claim 1, wherein the semiconductor light sources are arranged at a front end of a hand-held light curing device.

14. The light curing device as claimed in claim 1, wherein a light-conducting element is arranged in the light exit direction after the semiconductor light sources, said light-conducting element is in the form of a light-conducting rod.

15. The light curing device as claimed in claim 1, wherein the semiconductor light sources emit light at a wavelength of 350 to 480 nm and wherein at least two adjacent light sources emit light of different wavelength.

16. The light curing device as claimed in claim 1, wherein two to five reflector bodies are arranged adjacent to one another on a common substrate (20).

17. The light curing device as claimed in claim 1, wherein the light curing device comprises at least one sensor arranged on the substrate or connected with the substrate.

18. The light curing device as claimed in claim 1, wherein the individual reflector bodies are mounted on the common substrate, wherein the openings on the light emitting side of each individual reflector body are located in one plane, wherein said openings of each of the individual reflector bodies comprise a substantially circular shape, and wherein said openings do not intersect.

\* \* \* \* \*